United States Patent [19]

Nablo

[11] 4,252,413

[45] Feb. 24, 1981

[54] METHOD OF AND APPARATUS FOR SHIELDING INERT-ZONE ELECTRON IRRADIATION OF MOVING WEB MATERIALS

[75] Inventor: Sam V. Nablo, Lexington, Mass.

[73] Assignee: Energy Sciences Inc., Woburn, Mass.

[21] Appl. No.: 948,999

[22] Filed: Oct. 5, 1978

Related U.S. Application Data

[63] Continuation-in-part of Ser. No. 940,034, Sep. 6, 1978, which is a continuation of Ser. No. 742,134, Nov. 15, 1976, abandoned, which is a continuation of Ser. No. 530,942, Dec. 9, 1974, abandoned.

[51] Int. Cl.[3] .................... G01M 23/00; A61K 27/02

[52] U.S. Cl. .................................. 250/310; 250/306; 250/359; 250/440; 250/492 R; 250/515

[58] Field of Search ........... 250/492 R, 492 A, 492 B, 250/324, 310, 358, 359, 325

[56] References Cited

U.S. PATENT DOCUMENTS

| | | | |
|---|---|---|---|
| 3,564,238 | 2/1971 | Martin | 250/492 B |
| 3,654,459 | 4/1972 | Coleman | 250/492 B |
| 3,676,673 | 7/1972 | Coleman | 250/492 B |
| 3,980,889 | 9/1976 | Haas et al. | 250/492 R |
| 4,020,346 | 4/1977 | Dennis | 250/358 R |
| 4,143,118 | 3/1979 | Laing | 250/325 |

*Primary Examiner*—Harold A. Dixon
*Attorney, Agent, or Firm*—Rines and Rines, Shapiro and Shapiro

[57] ABSTRACT

This disclosure is concerned with novel techniques for shielding electron-produced scattered radiation in systems wherein a web or sheet is passed longitudinally through an electron irradiation processing region or zone, through the use of a shielded enclosure comprising longitudinally extending shielded-wall collimator slots operating in conjunction with cavity shield traps and critical angles of web-guiding inlet and outlet feed that insure minimal irradiation escape while providing a minimal volume for oxygen-limiting in the irradiation processing zone.

20 Claims, 5 Drawing Figures

Figure 1:
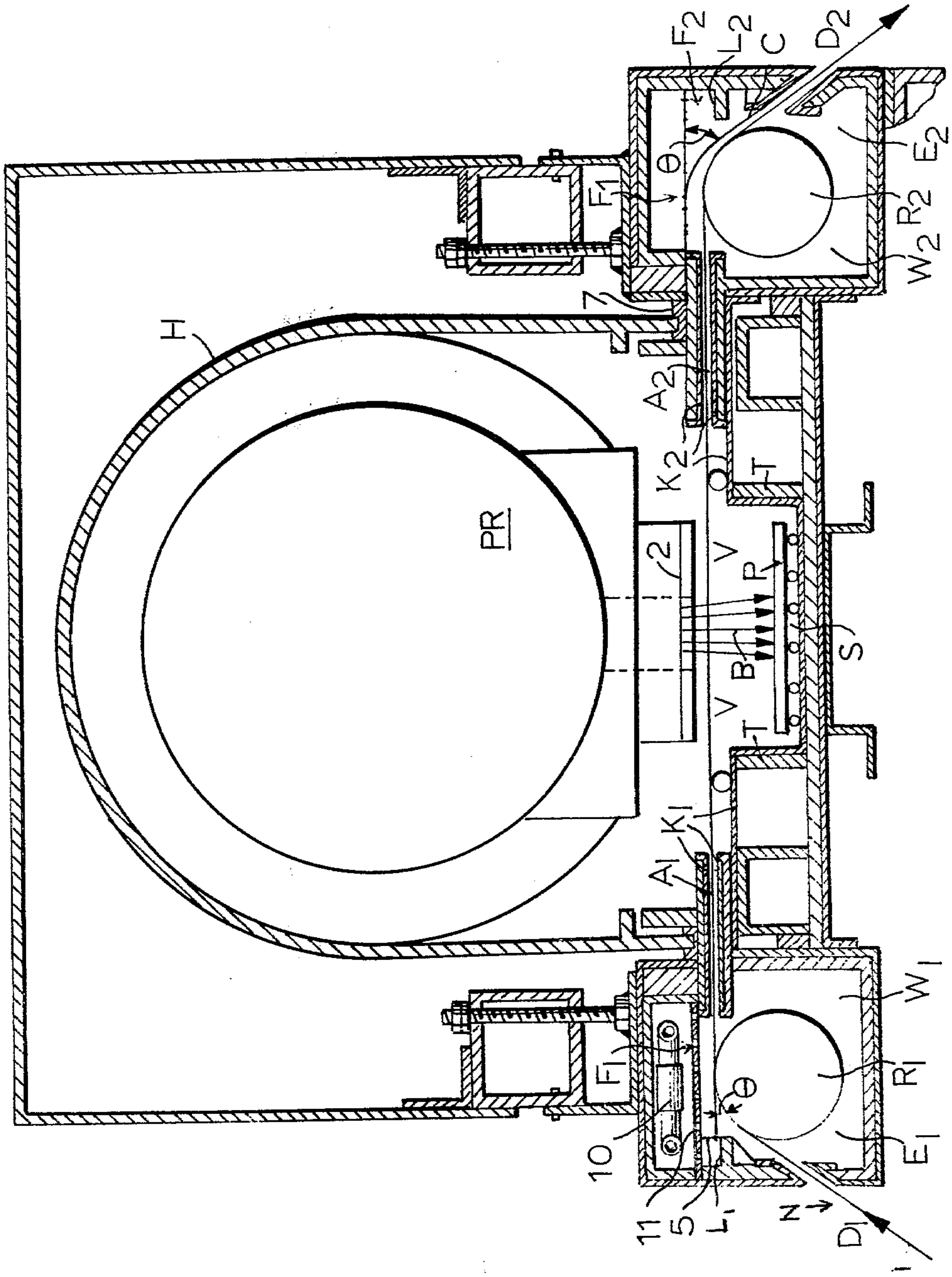

METHOD OF AND APPARATUS FOR SHIELDING INERT-ZONE ELECTRON IRRADIATION OF MOVING WEB MATERIALS

This application is a continuation-in-part of U.S. patent application Ser. No. 940,034, filed Sept. 6, 1978, in turn a continuation of application Ser. No. 742,134, filed Nov. 15, 1976, now abandoned and in turn a continuation of parent application Ser. No. 530,942, filed Dec. 9, 1974 now abandoned.

The present invention relates to methods of and apparatus for shielding inert-zone electron irradiation of moving web materials, including sheet materials themselves to be irradiated, or coatings thereon, or materials carried thereby to be processed, all generically referred to herein as webs or surfaces to be irradiated.

One of the major barriers to the widespread industrial use of the attractive advantages of the use of energetic electrons (energies>20 keV) for the completion of polymerization in free radical cured systems, for the cross-linking or degradation of various natural and synthetic polymers, and for the surface and bulk sterilization of materials, indeed, has been the difficulty of the introduction of the product to the electron processor or irradiator in a continuous manner, usually at high production-line speeds (e.g. at 30 m/minute to 500 m/minute).

This problem arises from the nature of the energy source. When energetic electrons stop in material, the relatively unpenetrating particle (electron), as it slows down, dissipates some of its energy in the form of penetrating photons (bremsstrahlung), and through the excitation of characteristic X-rays from the atoms of the material with which it interacts. The resultant source of penetrating x or photon radiation is difficult to confine due to its great penetrability in solid matter. As a consequence, on-line continuous application of electron curing has heretofore seemed impracticable. Processes which have been developed for wire and cable, polyethylene crosslinking and surface coating curing applications, have been accomplished with vault or volume shielding of the entire system-an approach quite incompatible with most high-speed line-curing requirements. And tray-fed self-shielded equipment for rigid products, as described, for example, by Carl Hoffman, "Shielding and Safety Requirements", Rad. Phys. and Chem., 9, 131–145 (1977), are completely unsuited to the flexible web problems of the present invention and the production techniques therein required.

The techniques of the present invention, however, have been developed and successfully used for the continuous, hazard-free introduction of material from the ambient environment, into the treatment zone of such an electron processor, and then back into the ambient environment. Since such a system must simultaneously satisfy the requirements of external environmental radiation safety, environmental control of the process zone and of the region external to the processor during continuous operation, safe handling of the product during its entrance, transit and exit from the processor, as well as ready maintainability, all of these factors must be included in the design and engineering of this critical part of the total system. The techniques underlying this invention have been developed specifically for the continuous treatment of product at ambient pressures, either in air or in an oxygen-depleted environment where such inerting is required to reduce scavenging of free radicals near or at the surface of the coating or polymer to be cured. The invention, accordingly, is also concerned with the necessity for oxygen limitation in the processing or irradiation region, station or zone, such that negligible ozone can be generated by secondary reflections and scatter, in addition to preventing the escape of X-rays and other radiation resulting from reflections and scatter in the system—particularly where moving webs must pass through the processing or irradiation zone.

Where the electrons are produced as a linear strip, as with the aid of the preferred apparatus for generating relatively low electron-beam voltages (50–250 KV, for example) described in U.S. Pat. Nos. 3,702,412; 3,745,396 and 3,769,600, these problems are compounded since radiation lobes are generated in the plane of the product surface since the bremsstrahlung generated by the stopped beam at these energies is roughly isotropic. Hence, there are relatively intense photon levels generated longitudinally forward and rearward of the web as it passes by the transverse electron-pervious window of the electron beam generator or processor. It is more particularly to the solution of problems arising with such and similar structures, that the invention is primarily directed, though the novel techniques herein are also useful in other energetic electron beam systems of the scanned or unscanned types, pulsed or direct-current, as described, for example, in U.S. Pat. Nos. 3,440,566; 3,588,565 and 3,749,967.

An object of the invention, accordingly, is to provide a new and improved method of, and apparatus for, shielding inert-zone electron irradiators of moving webs and the like, particularly, though not exclusively where significant longitudinal scatter-lobes are generated, as with linear electron beams; and to effect such shielding with constructions that enable the use of minimal volumes and sizes of processing zone wherein inert media are required or ozone escape to be prevented.

A further object is to provide novel shielding structures suitable for production-line treatment of sheet material and the like, and of more general applicability, as well.

Other objects will be pointed out hereinafter and are more clearly delineated in the appended claims.

Figure 2A:
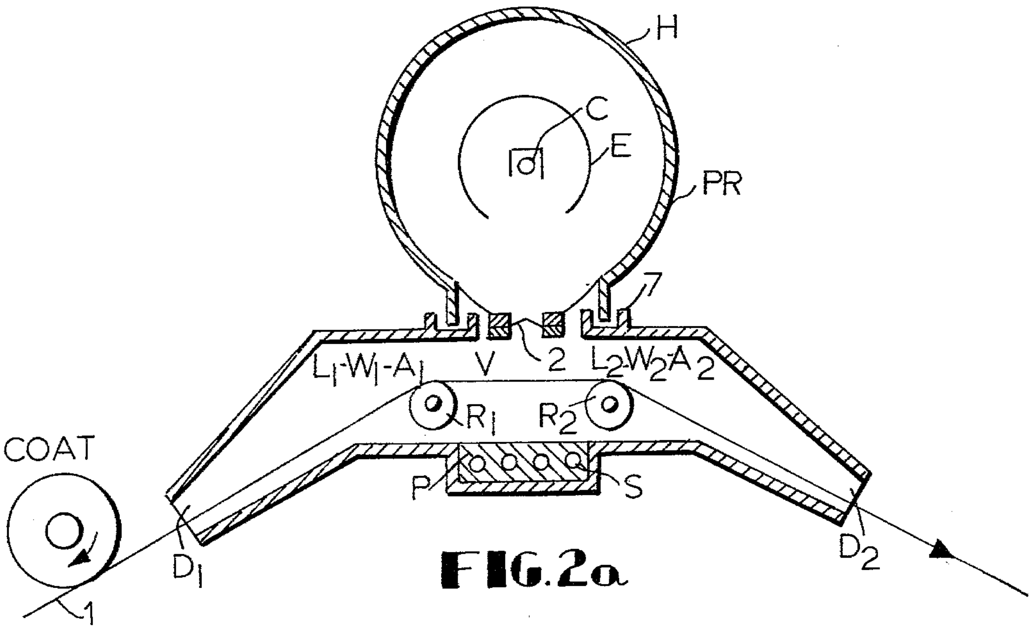
Figure 3:
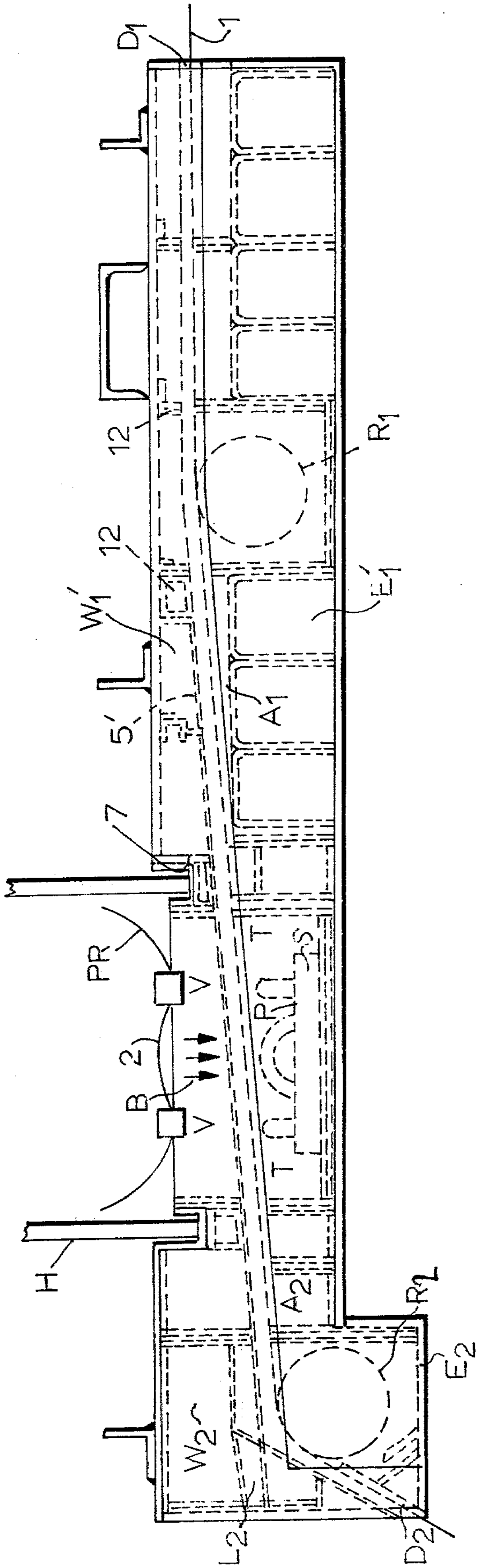
Figure 4:
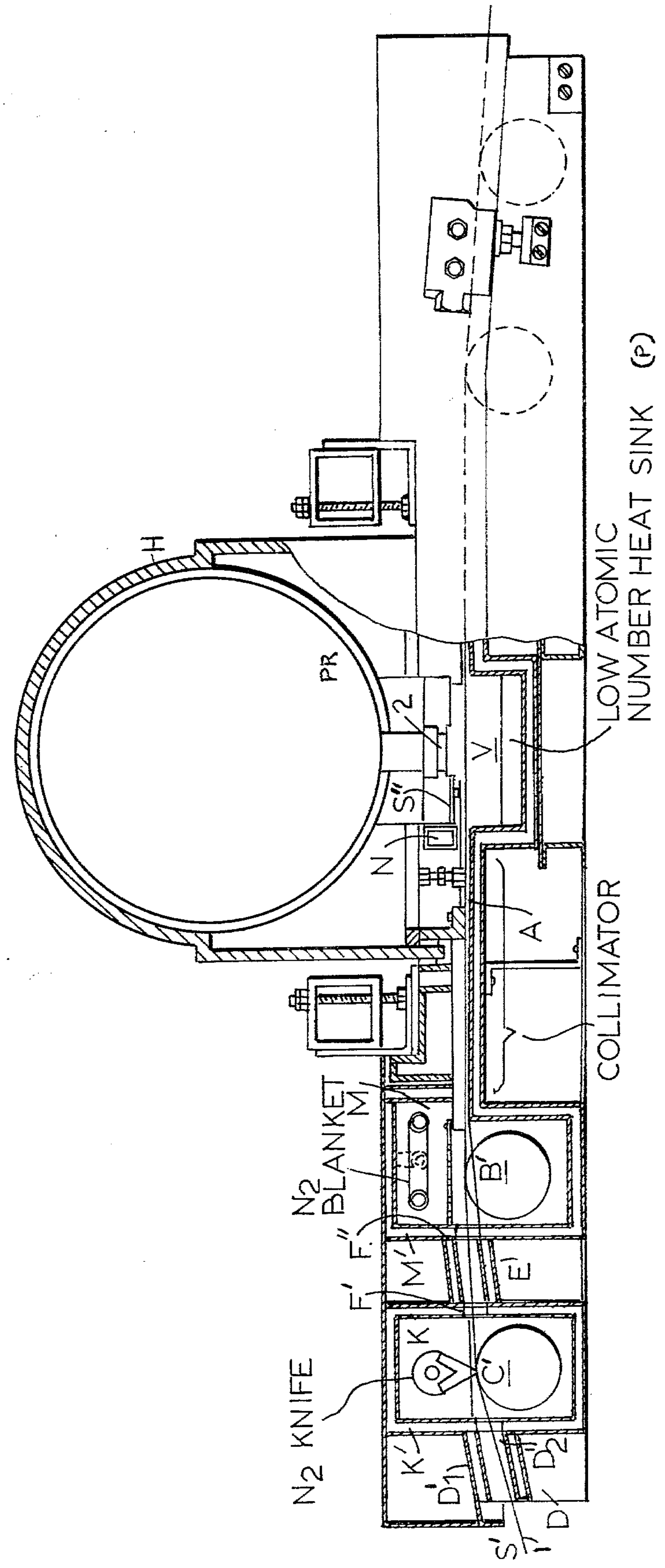

The invention will now be described with reference to the accompanying drawings, FIG. 1 of which is a longitudinal section of a preferred embodiment of the invention employing the novel method underlying the same;

FIGS. 2(A) and (B) are schematic diagrams of applications of the apparatus of FIG. 1; and FIGS. 3 and 4 are views similar to FIG. 1 of modifications.

In summary, from one of its important aspects, the invention embraces an apparatus for passing a web through an oxygen-limited electron irradiation zone and for shielding against scattered radiation, having, in combination, a longitudinally extending shielding enclosure provided with inlet and outlet regions connected by an intermediate zone at which the electron irradiation is to be concentrated; means for generating and directing electron beam radiation through an electron-pervious window disposed along the intermediate zone and serving as a wall of the zone; means forming an opposing wall along the intermediate zone comprising a shielded box radiation trap provided with cooling means; each of said inlet and outlet regions comprising parallel shielded wall surfaces forming longitudinally extending slots that collimate radiation scattered therealong outward from the irradiation intermediate zone; shielded cavity trap means disposed at said inlet and outlet regions to receive radiation scattered outward along the collimating slots from said intermediate zone; means for feeding a web to the inlet region collimating slot and longitudinally through the same, and thence longitudinally between the said window and shielded box through the said intermediate zone and then along the outlet region collimating slot to exit therefrom; and means for providing an oxygen-restricted atmosphere within said zone. Preferred details are hereinafter presented.

A common feature underlying the machinery of the invention, suitable for the treatment of two-dimensional or web surfaces, is that the energetic electrons all stop in a plane, either as defined by the product when in use, or as defined by a cooled heat sink for those electrons which were not stopped in the product itself. As these particles are stopped, penetrating bremsstrahlung or X-rays are produced, increasing quadratically with increasing atomic number of the medium in which the electrons decelerate. For the relatively low energies here-involved for most electron processing ($\leqq 300$ keV), particularly where flexible web is involved, this energy loss is directly dependent upon electron energy, and the radiation pattern is reasonably isotropic. The before-mentioned intense radiation lobes occurring along the plane of the product or heat sink which has defined the bremsstrahlung of photon source must not be allowed to reach the region exterior to the processor.

A secondary consideration of electron loss in such systems is the high probability of electron backscatter within the system, so that bremsstrahlung is created in other parts of the shield configuration due to these scattered primaries. In this energy range, it has been shown (e.g. WRIGHT, K. A. and TRUMP, J. G., "Back Scattering of Electrons from THICK TARGETS", J.A.P. 33, 687, 1962) that the backscatter is relatively independent of primary energy, but it is very sensitively dependent on atomic number of the scatterer. The primary or scattered primary electrons have a limited range in air, so they can normally never reach the region exterior to the processor. Nevertheless, multiple scattering can lead to remote bremsstrahlung generation which must be considered, and the dependence of electron multiple scattering on the atomic number of the scattering medium must be considered.

A final and most important consideration of system shielding is the Compton scattering of the penetrating photons (bremsstrahlung) generated in the stopping of the direct or scattered primaries. The process is described quite exactly by the Klein-Nishina theory of Compton scatter (see, for example, C. M. Davisson and R. D. Evans, Rev. Mod. Phys. 24, 1952).

Based upon these radiation/electron absorption and scattering considerations, the general features of a product-handling shield geometry constructed in accordance with the present invention include the following considerations:

(1) Electron energy must be kept as low as possible to reduce the amount of bremsstrahlung generated per unit of electron charge delivered from the processor.

(2) The electron stream must stop in a low atomic number absorber within the shield; if not the organic coating or the like that is to be cured, then a low atomic number surface which can also serve as a waste heat sink.

(3) The electron stream must be stopped in a trap so that the isotropic bremsstrahlung generated can only escape by multiple scatter.

(4) The escape slots for the primary photons of the bremsstrahlung spectrum must subtend as small a solid angle as possible at the plane of electron stopping. Product guide slots, moreover, have the further advantage of isolating the processing, irradiating or treatment zone so that it has a relatively low gas conductance to the exterior ambient environment, thereby permitting effective inerting of the treatment zone with relatively small gas flow rates, even at high product speeds.

(5) The bremsstrahlung which does escape from the primary process volume must be trapped in labyrinths to preclude further Compton-scattered photons from reaching the external environment.

(6) Scattering surfaces must be of a low atomic number material to reduce scatter, characteristic X-ray production and photo-electron production.

(7) The web or sheet product must undergo some angular change in direction of motion ($\theta$) which eliminates the large forward-scattered Compton component from reaching the external working environment, as well as permitting an in-line labyrinth and cavity absorber.

(8) The product access aperture must subtend as small an angle as possible at primary apertures so that scattered radiation will be unable to reach the external environment.

(9) Thin low atomic number absorbers are used to reduce the fluence of scattered electrons from the primary scattering and absorbing surfaces in the shield assembly.

A preferred shielding assembly embodying these features is shown in FIG. 1, such being adapted particularly for use with a 50 mA-150 kV linear-strip beam processor of the type described in said U.S. Pat. No. 3,702,412.

Referring to FIG. 1, a flexible web or surface of material-to-be-irradiated is shown at 1, introduced at a product access or inlet aperture $D_1$ subtending a small angle to the vertical (item (8), above) in a radiation-shield inlet region enclosure $E_1$, shown as an inlet slot oriented at an angle to the horizontal of about 60°. The web product 1 undergoes an angular change in direction of motion $\theta$ (item (7)), as it continues over an idler roll $R_1$ and along a longitudinally extending parallel-plate slot $A_1$ (horizontal) into the intermediate processing or irradiation zone, region or volume V, past the electron-pervious window 2 (bounding the region V at the top wall) of the linear-strip low-energy electron beam generator or processor PR before-described and illustrated in the first-named Letters Patent, (item (1)), whence it receives the electron-beam radiation as a transverse strip beam, schematically illustrated by the downward arrows B. The processor PR is illustrated as mounted within a basic head shield housing or mounting H, detachably secured in a U-shaped radiation trap 7 externally transversely and longitudinally surrounding the shield enclosure containing the irradiation zone V. The irradiated web or material then continues horizontally through a similar longitudinally extending parallel plate slot $A_2$, and then over an idler roll $R_2$, exiting at a similar angle to the entrance angle, through an outlet aperture $D_2$ in the right-hand outlet region enclosure $E_2$.

In the intermediate processing, irradiating or treatment zone, region or volume V, the U-shaped radiation trap box T-T has angulated walls that bound the lower portion of the irradiation zone or volume, satisfying the trapping criterion of item (3), above. A low atomic number plate P (as of aluminum) serves as the opposing bottom wall of the trap T-T, covering or facing a heat sink or cooled plate S therebelow, such as water-cooling pipes (item (2)). The slots $A_1$ and $A_2$, by virtue of their construction parallel to the plane of the web as it passes the processor PR, subtend a very small solid angle at the plane of the electron-stopping at the web and at the plate P (item (4)), serving to collimate radiation scattered therealong. This construction also enables isolation of the treatment zone or volume V, providing a relatively low gas conductance to the exterior ambient environment outside $D_1$ and $D_2$, thereby permitting effective inerting of the zone V with relatively small gas flow rates (such as nitrogen), even at high line speeds of transit of the web 1. The collimating slots $A_1$ and $A_2$ at the respective inlet and outlet regions may be constructed of aluminum-coated lead and, as before explained, reduce the radiation streaming outward, laterally toward the inlet and outlet regions from the intermediate irradiation zone V. The paths that such Compton-scattered photon radiation may take through the collimating slots $A_1$ and $A_2$ terminate in labyrinths $L_1$ and $L_2$, faced with thin, low atomic-number absorbers $F_1$ and $F_2$ respectively, as of covered or faced lead, the cavities $W_1$ and $W_2$ thereat serving as radiation trap cavities (items (5) and (9)). The scattering surfaces at $K_1$ and $K_2$, moreover, associated with slots $A_1$, $A_2$, etc., are also of low atomic number material thus to reduce scatter, X-ray and photo-electron production (item (6)); in particular, to reduce radiation generation by electrons scattered laterally by the trap T-T, window 2 and/or web product. The inlet region cavity trap labyrinth $L_1$-$F_1$, etc., outwardly spaced from the collimating slot $A_1$, may be provided with an aluminum window cover 5 to close off the same and stop reflections in the cavity, though permitting the entry of scattered radiation.

In practice, the angles of entrance and exit of the web 1 (greater than a few degrees and of the order of 60° in preferred application) are adjusted thus to "see" as little scattered radiation from the collimating slots $A_1$ and $A_2$ and end trap cavities; the invention providing for minimum radiation processing volume and minimum volume required for inerting or ozone elimination. The inert gas may, for example, be applied through a manifold 10 and a distributing baffle 11 therebelow at the top of the left-hand terminal enclosure $E_1$-$W_1$. An airknife, such as a high-pressure nitrogen nozzle N may be disposed near the inlet guide $D_1$ to strip off the boundary layer of air carried by the web 1.

The assembly of FIG. 1 has been found to reduce the primary bremsstrahlung level in process cavity V from $10^8$ rads/second, to a secondary bremsstrahlung level of $\sim 10^2$ rads/hour in the secondary product-handling cavities $W_1$ and $W_2$, to a tertiary bremsstrahlung level of $\sim 10^{-4}$ rads/hour in the external environment beyond the product access and exit slots $D_1$ and $D_2$.

Figure 2B:
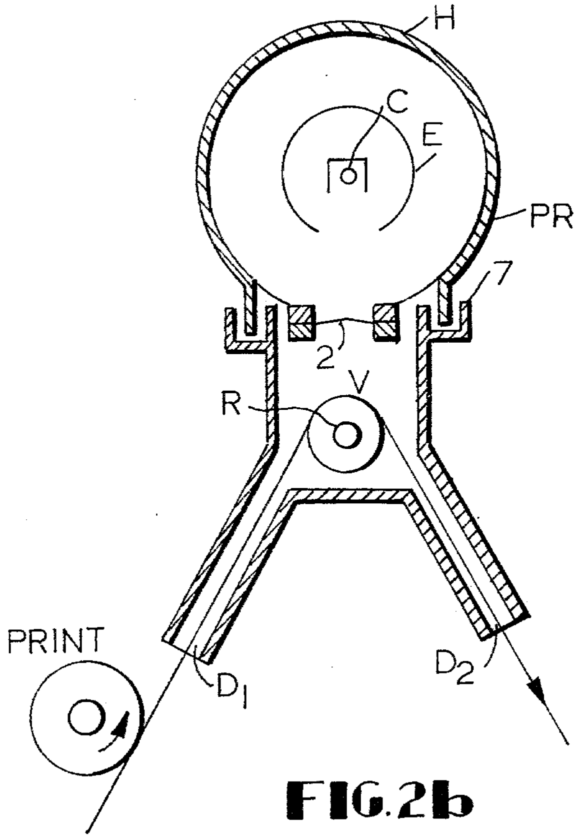

Other variants of this design geometry are shown more schematically (and in outline and not detailed form) in FIG. 2. FIG. 2(A) outlines the configuration of FIG. 1, shown applied to, for example, curing coatings on sheet material. The transversely extending cathode C and grid E of the processor PR are schematically illustrated in alignment with the window 2. The variant of FIG. 2(B), however, is most appropriate for high-speed web handling on a cooled single roller R, as for curing inks and the like, and with somwhat steeper-angle web entrance and exit. Such an assembly embraces many of the features of FIG. 1, schematically referenced, but reduces the flux in the primary zone V from $10^8$ rads/hour to $10^{-4}$ rads/hour at the exterior surface of the exit slots $D_1$ and $D_2$ and the external working environment.

These concepts have been reduced to practice in machinery of 30 cm, 1.25 meters and 1.70 meters in transverse electron-beam strip width. All of these systems used the techniques herein taught to provide self-shielded machinery with radiation level reductions of from $10^9$ rads/second in the region V immediately under the processor window 2, to $3.10^{-7}$ rads/second in the region immediately adjacent to the product access slot $D_1$ or $D_2$. This level is somewhat below the figure of 2.5 mr/hour (or $7 \times 10^{-6}$ rads/second) specified by OSHA for a hand-access region in an "unrestricted" area (ref.: OSHA 1910.96, p. 10518, FR 36, #105, May 29, 1971).

In accordance with the present invention, thus, a system is provided which permits the continuous introduction of flexible web directly into and from the primary process zone of an electron processor operating in the energy range of, say, 100–500 kilovolts and at average dose rates from $10^5$–$10^9$ rads/second, and which so isolates that process zone from the external environment that the radiation levels are reduced by 14–16 orders of magnitude in the region immediately adjacent to the electron processor or its associated product-handling system. This self-shielded product-handling system provides for the continuous introduction to, and removal of flexible or rigid samples from, the electron processor, while providing an inert or controlled environment in the process zone with low gas conductance to the external environment, and for continuous use under ambient external conditions. While most useful in direct-current electron-strip beam applications in the 100 kilovolt to 500 kilovolt region, the invention is suitable with repetitively pulsed conditions at instantaneous electron dose rates at $10^{14}$ rads/second in the process zone (as in cold cathode systems); with swept beam conditions at instantaneous electron dose rates to $10^{11}$ rads/second in the process zone; and with continuous beam illumination at average electron dose rates to $10^9$ rads/second in the process zone. The construction, moreover, is symmetrical and modular and separable, so that the system comprising the terminal regions $E_1$-$W_1$ etc., $E_2$-$W_2$, etc. and the intermediately connected shielded box trap T-T, etc. may be separated from the electron processor PR (H) at will, for access, and can be readily mated to the processor with interleaving shielding sections 7 (FIGS. 1 and 2) to provide a radiation-tight interface, complying with the requirements for use of such systems in an unrestricted area.

The self-shielded web-handling systems of the invention are particularly suitable for use with flexible products (paper, film and foil, laminates thereof or unslit packaging constructions) up to 5 mm in thickness, and at electron energies from 50 to 250 keV, and at product speed from 5–5000 meters/minute. The average electron power fluxes in the curing zone range from 10–200 watts/cm$^2$. Self-shielding is readily accomplished with the use of lead or other high atomic number material permanently clad to the process head and web-handling system, typically 6 mm thickness at 175 keV and up to 1 cm in thickness at 250 keV, with male shielding fittings on the processor head and an interleaving recess or female fitting 7 on the product handling assembly, as before mentioned.

The before-mentioned reduction of radiation levels by about 15 orders of magnitude or more in the self-shielded web handling assembly is thus accomplished by means of the collimation of the energetic primary bremsstrahlung, and its capture in a shielded labyrinth or recess, with a secondary, non-coplanar product access slot for continuous introduction and removal of the product from the processor.

While horizontal passage through the electron beam zone has been described, oblique non-horizontal passage is possible with primary radiation collimators directing the radiation into oblique collectors, permitting horizontal entrance of the product into the web-handling assembly, if desired. This is illustrated in FIG. 3, with entrance shown from the right, and oblique or inclined passage through the irradiation zone V, and an acute angle exit at $D_2$. An aluminum or other electron-pervious window 5' is shown facing the radiation cavity trap $W_1'$ in the right-hand terminal section or enclosure $E_1'$, and baffle steps 12 are provided for preventing multiple scattering along the web.

A preferred geometry is shown in FIG. 4 which has the further advantage of reducing the channel or aperture lengths required on the entrance and exit sides, and utilizes a double-angle change in the product motion, while preserving a horizontal presentation to the beam in the process zone under the window 2. Entrance (and exit) collimators D through which the product passes, terminate at primary roll C', while introducing a small angle change (typically about 5°) in the direction of product motion. Entrance collimator D is provided with recessed radiation traps $D_1'$ and $D_2'$ which prevent scattered radiation from streaming to the entrance (or exit) slots S' adjacent the irradiation zone V. After passing over roll C' the web 1 passes through radiation trap E and collimators F'-F" to roll B', where the second small angle change occurs. The web 1 then proceeds to process zone V via extended collimator A. This double-angle (arc-like) change permits a dramatic reduction in the radiation levels detectable at S' to levels of $10^8$-$10^9$ rads/second in V; with a very short entrance (i.e. window distance S'-V).

Rolls C' and B' may be replaced with rigid bars, or can be removed for lower speed (<300 fpm) applications. Another embodiment of this geometry for web would involve a gently curved arcuate slot from (rather than the roughly arcuate nature of the double-angle change), using no rollers or bars and interspersed collimators (A) and traps (D) along the length of the entrance or exit arcs.

As shown in this geometry of FIG. 4, a nitrogen knife K can be used above (or below) the web in cavity K' to strip the air boundary layer from the web at high speeds. In addition, a distributor or baffled plate M can be used to flood the product surface before entrance to V by using such a manifold assembly in cavity M'. Much more effective inerting is accomplished by using a sheet metal face over the radiation traps D and E so that the inerting gas flows at a higher velocity without turbulence over the length of the web as it enters treatment zone V.

An additional inerting embodiment is also shown in which the inert gas is admitted via manifold N to slot S" in the hold-down plate of the window 2. This technique permits the use of gas or convective cooling of window 2 with effective "pressurization" of the process zone V with the inert gas; i.e. due to the relatively low conductance of entrance and exit apertures.

In applications that do not require inerting, such as crosslinking or the curing of a laminating adhesive, the product handling assembly may be exhausted so that there is a continuous flow of air into the assembly that confines ozone generation therewithin and avoids the escape of ozone into the working environment. Typically, this involves the use of a radiation baffled duct in the assembly which is connected to an external exhaust fan via a flexible hose, not shown. A 2000 cfh blower and ducts cut, for example, into the top and bottom of duct extensions mounted on the shielded web handling assembly of the drawings, can keep the environmental ozone levels at less than 0.1 ppm, which is the OSHA limit for occupied areas (Paragraph 1910.93, "Air Contamination"). The invention is thus useful, also, where no inerting is required but the reverse process is applied; i.e. the low slot gas conductance system, is used with negative pressure in the treatment or irradiation zone to confine electron-produced ozone to the web handling assembly, and to restrict its flow to the external environment.

Further modification will also occur to those skilled in this art, and such are considered to fall within the spirit and scope of the invention as defined in the appended claims.

What is claimed is:

1. Apparatus for passing a web through an oxygen-limited electron irradiation zone and for shielding against scattered radiation, having, in combination, a longitudinally extending shielding enclosure provided with inlet and outlet regions connected by an intermediate zone at which the electron irradiation is to be concentrated; means for generating and directing electron beam radiation through an electron-pervious window disposed along the intermediate zone and serving as a wall of the zone; means forming an opposing wall along the intermediate zone comprising a shielded box radiation trap including angulated walls defining a box for stopping the electron beam at the intermediate zone, said box having within it a low atomic number plate upon which the electron beam radiation impinges and provided with cooling means; each of said inlet and outlet regions comprising parallel shielded wall surfaces forming longitudinally extending slots that collimate radiation scattered therealong outward from the irradiation intermediate zone; shielded cavity trap means disposed at said inlet and outlet regions to receive radiation scattered outward along the collimating slots from said intermediate zone; means for feeding a web to the inlet region collimating slot and longitudinally through the same, and thence longitudinally between the said window and shielded box trap through the said intermediate zone and then along the outlet region collimating slot to exit therefrom; and means for providing an oxygen-restricted or ozone-confining atmosphere within said zone.

2. Apparatus as claimed in claim 1 and in which said electron beam extends transversely across said web.

3. Apparatus as claimed in claim 2 and in which the shielding of said traps and wall surfaces comprises lead faced with a low atomic number surface such as aluminum.

4. Apparatus as claimed in claim 2 and in which at least one of said cavity trap means is disposed spaced from the end of its adjacent collimating slot.

5. Apparatus as claimed in claim 2 and in which said electron beam directing means is contained within a transversely extending shielding housing mounted upon said enclosure on each side of said irradiation zone.

6. Apparatus as claimed in claim 1 and in which said cooling means comprises water-cooled means covered by said plate and disposed at the base of said box trap.

7. Apparatus as claimed in claim 1 and in which the longitudinally extending slots have successive angle changes.

8. Apparatus as claimed in claim 1 and in which the longitudinally extending slots are arcuate.

9. Apparatus for passing a web through an oxygen-limited electron irradiation zone and for shielding against scattered radiation, having, in combination, a longitudinally extending shielding enclosure provided with inlet and outlet regions connected by an intermediate zone at which the electron irradiation is to be concentrated; means for generating and directing electron beam radiation through an electron-pervious window disposed along the intermediate zone and serving as a wall of the zone; means forming an opposing wall along the intermediate zone comprising a shielded box radiation trap provided with cooling means; each of said inlet and outlet regions comprising parallel shielded wall surfaces forming longitudinally extending slots that collimate radiation scattered therealong outward from the irradiation intermediate zone; shielded cavity trap means disposed at said inlet and outlet regions to receive radiation scattered outward along the collimating slots from said intermediate zone; means for feeding a web to the inlet intermediate zone; means for feeding a web to the inlet region collimating slot and longitudinally through the same, and thence longitudinally between the said window and shielded box trap through the said intermediate zone and then along the outlet region collimating slot to exit therefrom, said cavity trap means being disposed within terminal shielded sections containing inclined guides for directing the web at acute angles into and out of said enclosure; and means for providing an oxygen-restricted or ozone-confining atmosphere within said zone.

10. Apparatus as claimed in claim 9 and in which one of the said sections contains means for diffusing an inert medium into said channel.

11. Apparatus as claimed in claim 9 and in which air-knife means is directed upon the web entering the guide of the inlet terminal section.

12. Apparatus as claimed in claim 11 and in which the mounting comprises a housing the free edges of which are received within a transversely extending U-shaped radiation trap carried externally by the enclosure to the sides of said irradiation zone.

13. Apparatus as claimed in claim 6 and in which the said terminal section guides and web-feeding means and the shielded box trap are disposed as a unit forming one wall of the shielded enclosure and movable into juxtaposition with the opposing wall carrying the electron generating means and with a peripheral radiation trapping flange closing the same.

14. A method of minimizing electron-produced reflection and scatter radiation while providing a minimal volume zone for electron irradiation of a passing web and the like, that comprises, passing the web between an inlet and an outlet and longitudinally past an intermediate processing zone; directing a transverse line of electrons upon the web as it longitudinally passes along said region; trapping and suppressing electrons emerging on the other side of the web within said processing zone; collimating electron-produced scatter longitudinally outward in opposite directions from said zone toward the inlet and outlet; cavity-trapping the collimated scattered radiation; introducing the web at an angle to the direction of inlet collimation and exiting the same at an angle to the direction of outlet collimation with said angles adjusted to block the escape of such scatter; and inerting or providing ozone confining within said zone.

15. A method as claimed in claim 14 and in which a gas is blown upon the web as it passes between inlet and processing zone.

16. A method as claimed in claim 14 and in which the introducing and exiting steps each comprise successive angular changes.

17. A method as claimed in claim 16 and in which a gas blanket is provided upon the web following the angular changes.

18. A method as claimed in claim 16 and in which the introducing and exiting steps are along substantially arcuate paths.

19. Apparatus for passing a web through an oxygen-limited electron irradiation zone and for shielding against scattered radiation, having, in combination, a longitudinally extending shielding enclosure provided with inlet and outlet regions connected by an intermediate zone at which the electron irradiation is to be concentrated; means for generating and directing electron beam radiation through an electron-pervious window disposed along the intermediate zone and serving as a wall of the zone; means forming an opposing wall along the intermediate zone comprising a shielded box radiation trap provided with cooling means; each of said inlet and outlet regions comprising parallel shielded wall surfaces forming longitudinally extending slots that collimate radiation scattered therealong outward from the irradiation intermediate zone; shielded cavity trap means disposed at said inlet and outlet regions to receive radiation scattered outward along the collimating slots from said intermediate zone, the shielding of said traps and wall surfaces comprising lead faced with a low atomic number surface such as aluminum, said cavity trap means being bounded by said shielding and comprising a labyrinth faced with an electron-permeable window to close off the same but into which radiation scattered outward along the collimating slots may enter the cavity labyrinth; means for feeding a web to the inlet region collimating slot and longitudinally through the same, and thence longitudinally between the said window and shielded box trap through the said intermediate zone and then along the outlet region collimating slot to exit therefrom, said electron beam extending transversely across said web; and means for providing an oxygen-restricted or ozone-confining atmosphere within said zone.

20. Apparatus for passing a web through an oxygen-limited electron irradiation zone and for shielding against scattered radiation, having, in combination, a longitudinally extending shielding enclosure provided with inlet and outlet regions connected by an intermediate zone at which the electron irradiation is to be concentrated; means for generating and directing electron beam radiation through an electron-pervious window disposed along the intermediate zone and serving as a wall of the zone; means forming an opposing wall along the intermediate zone comprising a shielded box radiation trap provided with cooling means; each of said inlet and outlet regions comprising parallel shielded wall surfaces forming longitudinally extending slots that collimate radiation scattered therealong outward from the irradiation intermediate zone; shielded cavity trap means disposed at said inlet and outlet regions to receive radiation scattered outward along the collimating slots from said intermediate zone; means for feeding a web to the inlet region collimating slot and longitudinally through the same, and thence longitudinally between the said window and shielded box trap through the said intermediate zone and then along the outlet region collimating slot to exit therefrom, at least one of said cavity trap means being disposed within a terminal shielded section containing a guide for directing the web-substantially horizontally, with the web passing inclinedly through said zone; and means for providing an oxygen-restricted or ozone-confining atmosphere within said zone.

* * * * *